(12) United States Patent
Tice

(10) Patent No.: US 6,987,459 B2
(45) Date of Patent: Jan. 17, 2006

(54) PORTABLE COMBUSTIBLE GAS DETECTOR

(75) Inventor: Lee D. Tice, Bartlett, IL (US)

(73) Assignee: Honeywell International, Inc., Morristown, NJ (US)

( * ) Notice: Subject to any disclaimer, the term of this patent is extended or adjusted under 35 U.S.C. 154(b) by 62 days.

(21) Appl. No.: 10/351,271

(22) Filed: Jan. 24, 2003

(65) Prior Publication Data
US 2004/0145485 A1 Jul. 29, 2004

(51) Int. Cl.
G08B 17/10 (2006.01)

(52) U.S. Cl. .................. 340/632; 340/693.6; 73/23.31; 73/31.05; 73/35.15; 422/83; 422/94; 422/280

(58) Field of Classification Search ............... 340/632, 340/693.6; 73/31.05, 23.31, 35.15; 422/83, 422/94, 280
See application file for complete search history.

(56) References Cited

U.S. PATENT DOCUMENTS

| | | | | |
|---|---|---|---|---|
| 2,801,297 A | * | 7/1957 | Boxman et al. | 330/290 |
| 3,929,003 A | * | 12/1975 | Llewellyn | 73/61.72 |
| 4,485,666 A | * | 12/1984 | Higgins et al. | 73/23.2 |
| 4,542,640 A | * | 9/1985 | Clifford | 73/31.06 |
| 4,670,405 A | * | 6/1987 | Stetter et al. | 436/151 |
| 4,938,928 A | | 7/1990 | Koda et al. | |
| 5,034,192 A | | 7/1991 | Wrighton et al. | |
| 5,145,645 A | | 9/1992 | Zakin et al. | |
| 5,255,556 A | * | 10/1993 | Lobdell | 73/31.02 |
| 5,605,612 A | | 2/1997 | Park et al. | |
| 6,006,585 A | * | 12/1999 | Forster | 73/24.01 |
| 6,053,030 A | * | 4/2000 | Whynall et al. | 73/23.2 |
| 6,076,389 A | * | 6/2000 | Kaneko | 73/1.06 |
| 6,545,278 B1 | * | 4/2003 | Mottier et al. | 250/339.13 |
| 6,606,897 B1 | * | 8/2003 | Koyano et al. | 73/23.2 |
| 6,679,094 B2 | * | 1/2004 | Wang et al. | 73/1.06 |
| 6,687,005 B2 | * | 2/2004 | Kim | 356/437 |
| 2002/0177232 A1 | | 11/2002 | Melker et al. | |
| 2003/0004426 A1 | | 1/2003 | Melker et al. | |
| 2003/0052792 A1 | * | 3/2003 | Koyano et al. | 340/632 |

OTHER PUBLICATIONS

Electronic Super Sniffer, Engineering News, published on or before Aug. 11, 2000.
CYRANO Sciences, Inc. The Cyranose 320 Electronic Nose, User's Manual, Revision 180800; published on or before Aug. 31, 2000.

(Continued)

*Primary Examiner*—Daniel Wu
*Assistant Examiner*—Samuel J. Walk
(74) *Attorney, Agent, or Firm*—Welsh & Katz, Ltd.

(57) ABSTRACT

A portable detector of combustible or explosive gases incorporates a polymeric-type sensor or sensor array coupled to a programmed processor which carries out an evaluation of one or more signals from the sensor or array to evaluate the presence of combustible or explosive vapors. Non-polymeric sensors such as temperature sensors, humidity sensors and/or pressure sensors can also be incorporated and their outputs evaluated to compensate the outputs of the sensor or array of sensors. The detector can be housed in a sealed enclosure and energized by a battery.

16 Claims, 4 Drawing Sheets

OTHER PUBLICATIONS

The Practical Guide to the Cyranose 320™, Cyrano Sciences, Inc., Revision: A2, Sep. 26, 2000 23:45.

Jing Li, The Cyranose Chemical Vapor Analyzer, Chemical/Process, Aug. 2000.

Ioana Voiculescu, Mona Zaghloul, R. Andrew Mc Gill, Design and Modeling Of Microbeam Gas Sensor In CMOS Technology, published more than one year before filing date of present application.

Clifford K. Ho, Michael T. Itamura, Michael Kelley, and Robert C. Hughes, Review of Chemical Sensors for InSitu Monitoring of Volatile Contaminants, Sandia National Laboratories, Printed Mar. 2001.

Frank Zee and Jack Judy, MEMS Chemical Gas Sensor Using A Polymer-Based Array, published Jun. 7-10, 1999, Sendai, Japan.

Thomas M. Hawkins, Amjad N. Chaudry, and Paul J. Travers, Structure-Property Relationships in Conducting Polymer Gas Sensors, published more than one year before filing date of present application.

Yong Li, Raymond A. Adomaitis, Thomas J. Mc Avoy, Parameter Identification and Simulation of a Thin Film conducting Polymer Gas Sensor, Institute for Systems Research, published more than one year before filing date of present application.

* cited by examiner

FIG. 6A

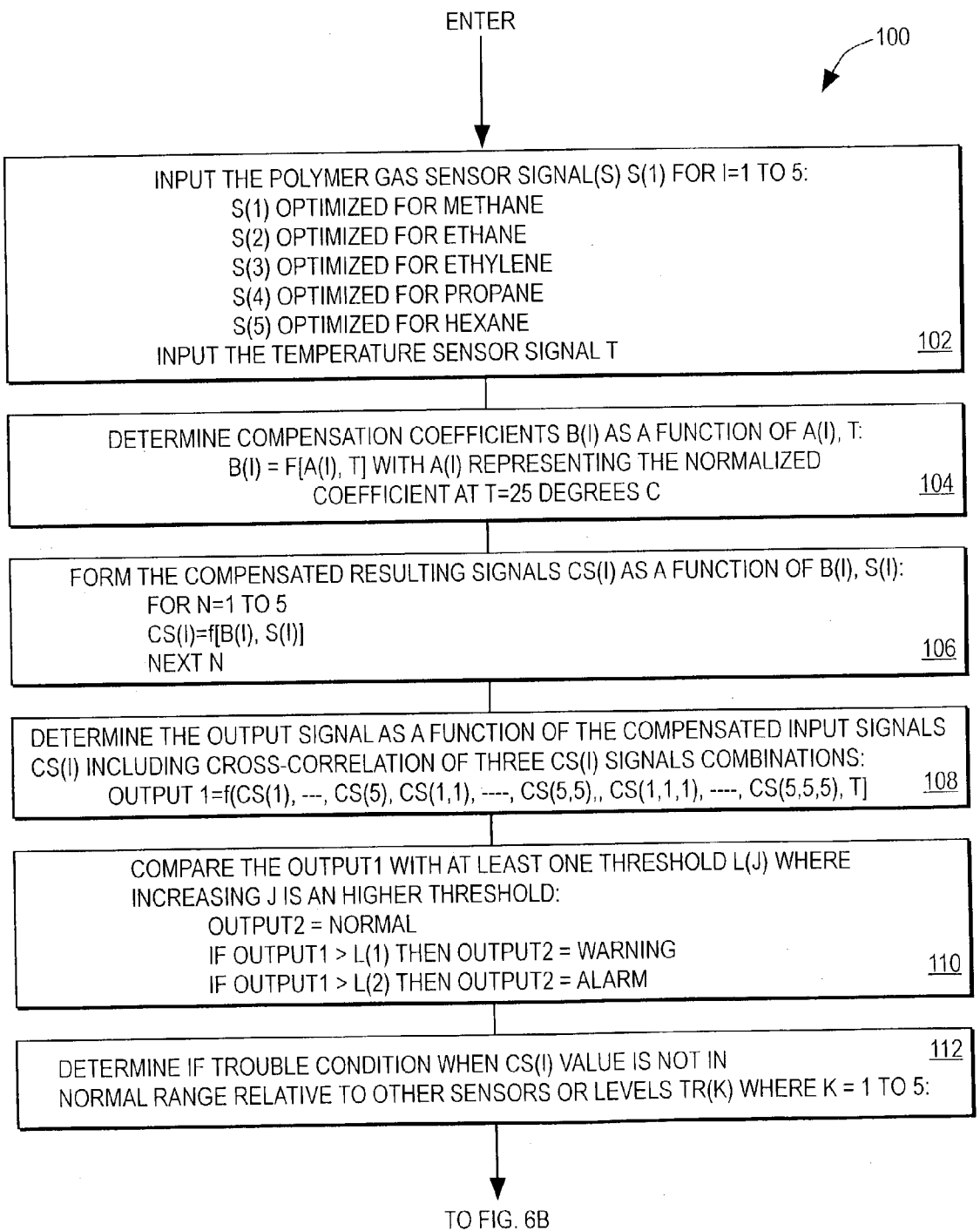

ENTER

100

INPUT THE POLYMER GAS SENSOR SIGNAL(S) S(I) FOR I=1 TO 5:
S(1) OPTIMIZED FOR METHANE
S(2) OPTIMIZED FOR ETHANE
S(3) OPTIMIZED FOR ETHYLENE
S(4) OPTIMIZED FOR PROPANE
S(5) OPTIMIZED FOR HEXANE
INPUT THE TEMPERATURE SENSOR SIGNAL T    102

DETERMINE COMPENSATION COEFFICIENTS B(I) AS A FUNCTION OF A(I), T:
B(I) = F[A(I), T] WITH A(I) REPRESENTING THE NORMALIZED
COEFFICIENT AT T=25 DEGREES C    104

FORM THE COMPENSATED RESULTING SIGNALS CS(I) AS A FUNCTION OF B(I), S(I):
FOR N=1 TO 5
CS(I)=f[B(I), S(I)]
NEXT N    106

DETERMINE THE OUTPUT SIGNAL AS A FUNCTION OF THE COMPENSATED INPUT SIGNALS
CS(I) INCLUDING CROSS-CORRELATION OF THREE CS(I) SIGNALS COMBINATIONS:
OUTPUT 1=f(CS(1), ---, CS(5), CS(1,1), ----, CS(5,5),, CS(1,1,1), ----, CS(5,5,5), T]    108

COMPARE THE OUTPUT1 WITH AT LEAST ONE THRESHOLD L(J) WHERE
INCREASING J IS AN HIGHER THRESHOLD:
OUTPUT2 = NORMAL
IF OUTPUT1 > L(1) THEN OUTPUT2 = WARNING
IF OUTPUT1 > L(2) THEN OUTPUT2 = ALARM    110

DETERMINE IF TROUBLE CONDITION WHEN CS(I) VALUE IS NOT IN    112
NORMAL RANGE RELATIVE TO OTHER SENSORS OR LEVELS TR(K) WHERE K = 1 TO 5:

TO FIG. 6B

PORTABLE COMBUSTIBLE GAS DETECTOR

FIELD OF THE INVENTION

The invention pertains to portable detectors of combustible or explosive gases. More particularly, the invention pertains to portable gas detectors which incorporate one or more polymeric-type gas sensors.

BACKGROUND OF THE INVENTION

It has been recognized that it is desirable to be able to monitor a variety of different types of gas concentrations in the ambient atmosphere in a given region. Examples include environmental monitoring such as detecting toxic or otherwise dangerous gases that can result from spills or leaks, or, monitoring gases in a variety of industrial process settings such as beverage manufacture, food manufacture and the like. Sensors of human generated odors or vapors or, exhaled breath have been used for medical diagnosis or analysis. Interest in other types of chemical gas monitoring grows out of wanting to detect dangerous circumstances such as leakage of combustible or explosive gases as might be released in a fire, or, explosion as well as gases expelled from various kinds of explosives such as land mines and the like.

Known systems for monitoring on-going processes often compare current process signatures to a signature associated with an optionally functioning process. Such comparisons are effective and useful where what is required is to carry out the process to produce a result as close as possible to that produced by an optionally functioning process. However, not all monitoring corresponds to this model.

Particularly in circumstances of potential danger such as when dealing with combustible or explosive gases, as well as explosive materials themselves, it would be desirable to have available compact and light weight detectors which could be easily carried or worn by personnel in the region of interest. Such detectors preferably would be battery powered with extended lifetimes due to relatively low power requirements of the detector. Additionally, it would be preferable if such detectors could provide readings with a relatively high degree of reliability so as to minimize false positives while at the same time reliability indicating the presence of dangerous levels of the relevant gas.

DETAILED DESCRIPTION OF THE EMBODIMENTS

Figure 1A:
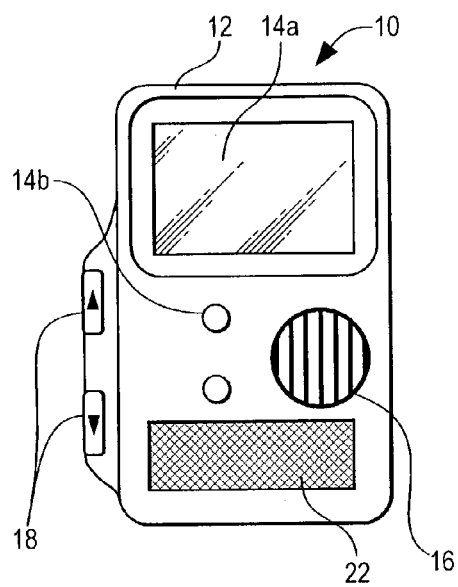
FIG. 1A is a front elevational view of a detector in accordance with the present invention.

While embodiments of this invention can take many different forms, specific embodiments thereof are shown in the drawings and will be described herein in detail with the understanding that the present disclosure is to be considered as an exemplification of the principles of the invention and is not intended to limit the invention to the specific embodiment illustrated.

A portable detector of combustible or explosive gases incorporates one or more polymeric-type sensors which are adapted for detecting the presence of predetermined combustive or explosive vapors. While such detectors incorporate a minimum of one polymeric-type sensor, preferably an array of polymeric-type sensors would be used to provide a recognizable pattern indicative of the presence of vapors of interest and/or the respective concentrations. Polymeric-type sensors in arrays can be configured to respond to a specific gas or gases of interest.

Recognition can be carried out using pattern recognition processing, threshold comparisons, or neural network-type analysis. Nonpolymeric-type sensors can be incorporated into the detector to compensate for variations of other environmental conditions such as temperature, humidity and/or pressure.

In one embodiment, an array of polymeric-type sensors can be combined with one or more nonpolymeric sensors, all of which are coupled to a programmed processor which carries out an analysis function. The circuitry can be energized by electrical energy from a battery.

The detector can be carried in a sealed housing which supports a display, such as a liquid crystal display alone or in combination with other types of display elements such as light-emitting diodes and/or the like. The enclosure can carry a filter to exclude airborne particulate matter and ambient water in a liquid form.

To further minimize any effects due to water that may migrate through the filter, a condenser can be located between the polymeric sensor or array of sensors and the filter. The enclosure can be sealed to exclude water, and to insure that the electrical components therein to not create a spark in an explosive atmosphere.

Detectors in accordance with the invention are small and light weight, for example with dimensions on the order of ½"×1"×1". They can be carried on a person's clothing, such as by being clipped to a pocket or collar. Additionally, they exhibit extended life-times due to low power requirements. They can cost effectively be configured as disposables with a preset lifetime. Polymeric-type sensor arrays usually display relatively high impedances which also helps reduce battery requirements.

Polymer type sensors are typically sensitive to many environmental conditions such as temperature, humidity, and altitude. This problem is solved in a disclosed embodiment by using external non-polymer sensors to automatically compensate the polymer sensors. Temperature can be monitored by an inexpensive thermistor, thermal-pile, wire, or p-n junction type sensor. Humidity can be monitored by either a non-polymer sensor conductivity or a polymer sensor that is specifically formulated to not be responsive to gases. Various pressure sensors exist in the marketplace that are relatively low cost.

Depending on the circumstances, the use of a thermistor alone may provide the information needed to perform the automatic sensitivity adjustment in the field. This adjustment can be performed by software routines that are executed within the detector.

The detector may be sealed to prevent contamination of the circuitry by elements in the environment. Sealing may be accomplished by an elastomeric, silicon, seal or rubber seal or any material that can be compressed to exclude contamination. It may be insert molded as part of a housing or other enclosure. It can seal against other enclosure surfaces or a common element such as a printed circuit board.

It is desirable that the sensor(s) be protected from liquid water that can be present in the environment for optimum performance. A first filter can be used to prevent liquid water from passing through to the sensors. Humidity will still pass through this filter. Treatment of the filter with water absorbing chemicals or a second filter can remove some water vapors. This first filter will also keep the polymer sensor(s) from being contaminated from particles in the environment.

Some users have temporary needs and may not want the expense of calibrating, maintaining, or keep track of these devices from an organizational standpoint. Being disposable relieves the user of these responsibilities.

Since a polymer sensor(s), thermistor, filter, and audible transducer are very small, it is possible to use a watch battery to power a detector that is very small, for example, the size of a postage stamp in width/length and very light weight. The depth is limited by the audible transducer and battery thickness and it may be less than a ¼ inch thick. This light weight detector may then be worn on clothing with the addition of a small clip or fastener.

A small switch can be used to turn it ON/OFF or it may be continually energized once activated and then expire after a predetermined operating life. Based upon the battery, the detector may run for several weeks or more before needing to be replaced. An indicator can be used to signal that the detector is functioning normally. This indicator can be visual, audible, or both.

Data processing software executable by a microprocessor in the detector, can in one embodiment, process the signals from the sensors and determine the concentration of combustible gases in the environment. A sampling technique can be used to turn the processor ON to measure the sensors, process sensor outputs, and then turn OFF until the next sampling time on a periodic basis. This reduces the current requirements of the detector and extends the life of the battery. The smaller the current, the smaller the battery. Battery capacity can be optimized with respect to operating life.

Polymeric-type sensors may have response characteristics that are slower than desired under certain conditions. Pre-stored mathematical routines can analyze these response characteristics and predict the actual concentration of the gas in the environment. Mathematical routines are known to those of skill in the art that can be implemented to perform this predictive function.

Methods of heating the sensor(s) can be used to drive the gases out of the sensor to produce a more rapid recovery. If the heating element is only used after an alarm has been indicated, then the power required to do so is only needed on the rare occurrence of an alarm. The heater can be manually controlled by the operator or can be automatic.

In summary, the advantages of polymeric sensors in disclosed detectors are (1) that they are very low in current requirements, 2) very small in size, essentially being flat, and 3) low in cost. Such sensors can be supervised by measuring their conductivity under normal and alarm conditions. This allows them to be monitored and to have an electronic self-calibrate capability to maintain sensitivity.

Figure 1B:
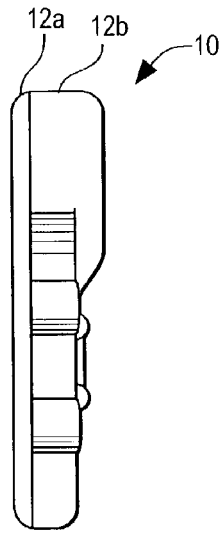
FIG. 1B is a side elevational view of the detector of FIG. 1A.

FIGS. 1A and 1B are front and side views respectively of a portable combustive or explosive gas detector 10 in accordance with the present invention. The detector 10 includes a housing 12 which can be formed of sections 12a, 12b which sealingly engage one another, defining an internal region 12c wherein the components of the detector 10 can be carried.

The detector 10 can incorporate visual output devices such as liquid crystal display 14a and illuminatable indicating element 14b which could be implemented as a light emitting diode or incandescent lamp. An audible output device such as a horn 16 can also be carried by the enclosure 12. Control buttons, knobs or switches 18 provide manually operable controls for purposes of turning the detector on or off or manipulating the information on the display 14a.

Figure 2:
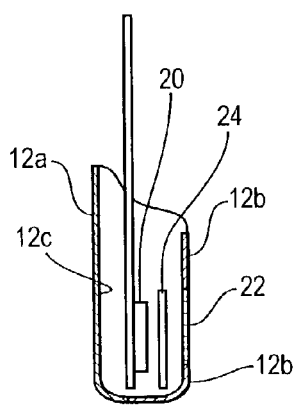
FIG. 2 is a partial view in section of the detector of FIG. 1B.

FIG. 2 is a partial view, in section, of the detector 10 illustrating one or more polymeric-type gas sensors 20 carried in housing or enclosure 12. The polymeric sensor(s) can be fabricated directly onto a printed circuit board containing the other electrical components.

A filter 22 is carried on enclosure 12 for purposes of excluding ambient airborne particulate matter such as bugs, dust, hair or the like along with water. To minimize any impact of inflowing water vapor, not withstanding the filter 22, a condenser 24 can be provided between the sensor or sensors 20 and filter 22.

Figure 3:
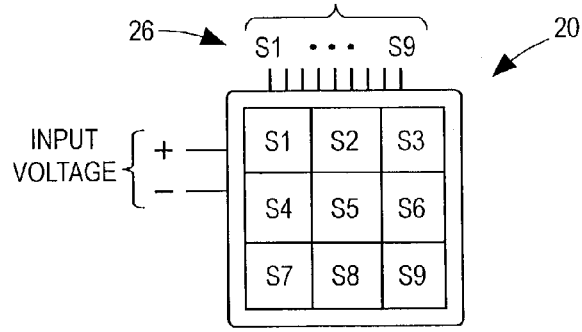
FIG. 3 is a schematic view of an array of polymeric-type sensors usable with the detector of FIG. 1A.

The sensor or sensors 20 can be implemented, for example as an array of different polymeric-type sensors, S1 . . . S9 best illustrated in FIG. 3. As will be understood by those of skill in the art, the various polymeric-type sensors S1 . . . S9 can be adjusted to respond differently to a selected combustible or explosive gas such as gasoline vapors, propane, methane, hydrogen or the like.

Figure 5:
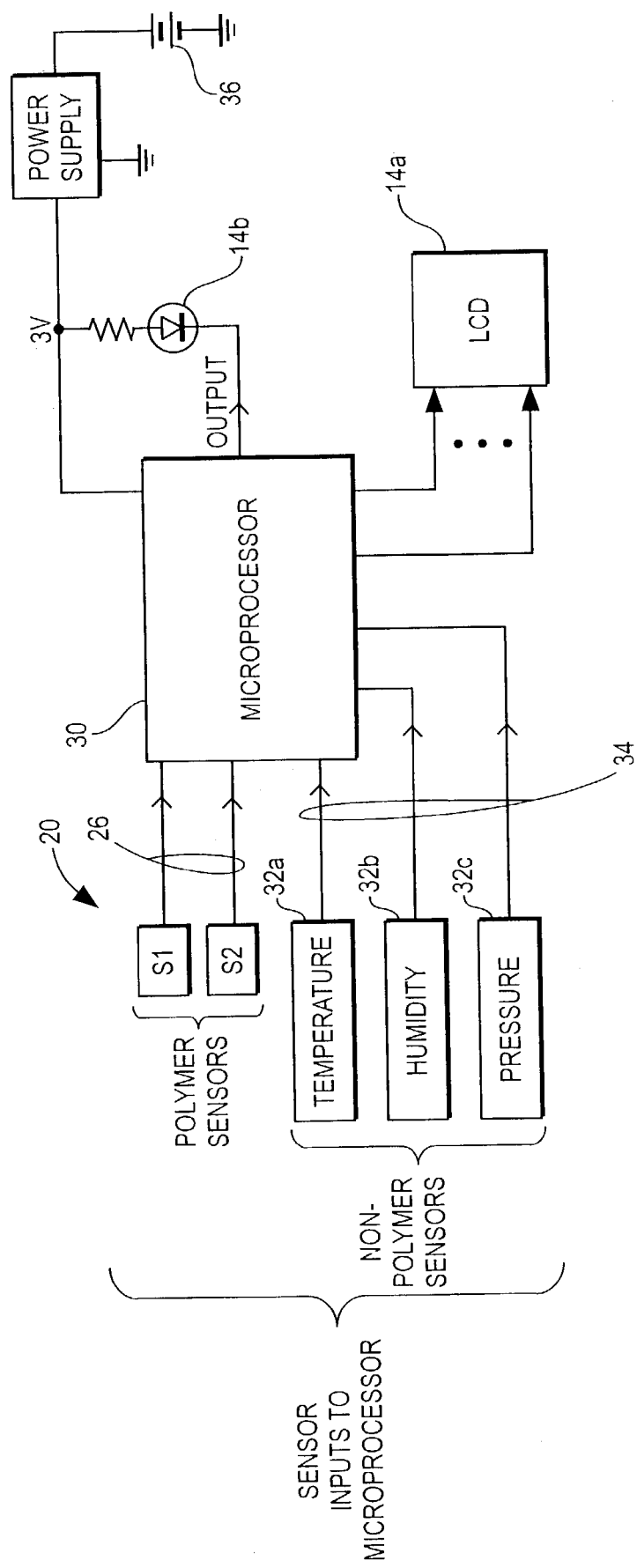
FIG. 5 is a schematic diagram illustrating an electronic control system for the detector of FIG. 1A.

Outputs 26 from the array of sensors 20 can be coupled to a control processor 30, best seen in FIG. 5, for analysis. Analysis can be carried out using a variety of processes including comparing output signals from one or more of the polymeric-type sensors S1 . . . S9 to one or more thresholds which represent various percentages of the relevant lower explosive concentration levels, carrying out pattern recognition processing based on a plurality of signals 26 from the sensor array 20 or alternately, neural network-type processing.

Figure 4:
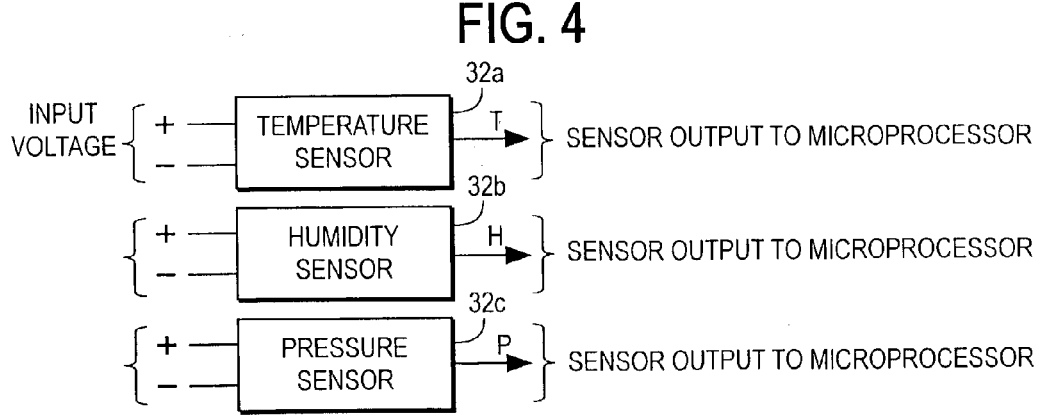
FIG. 4 is a schematic diagram of exemplary non-polymeric sensors usable with the detector of FIG. 1A.

FIG. 4 illustrates a variety of non-polymeric-type environmental compensating sensors usable in the detector 10 including temperature sensor 32a, humidity sensor 32b and pressure sensor 32c without limitation. It will be understood that other types of non-polymeric sensors could be incorporated into the detector 10 without departing from the spirit and scope of the present invention.

The detector 10, see FIG. 5, can include one or more pre-programmed processes carried out by pre-stored instructions executed by processor 30. These processes analyze outputs from the sensor array 20 alone or in combination with outputs from the sensors 32a, b, c for purposes of evaluating the presence or absence of one or more types of combustive or explosive vapors.

Those of skill in the art will understand that concentrations of different types of gases can be evaluated in accordance with appropriate respective criteria. It will also be understood that array 20 could include a first plurality of sensors Sa . . . Si, a second plurality of sensors Sj . . . Sn and even a third plurality of sensors Sp . . . Sv. Each plurality can be designed to respond to and provide a profile of different explosive vapors such as gasoline, natural gas, or hydrogen all without limitation.

As those of skill in the art will also understand, sensors in the array 20 can be configured so that some or all will produce substantially the same output in response to the same vapor or gas type and concentration. Alternately, they can be configured to produce predetermined different outputs to a common type of vapor and a common concentration.

The visual output devices display 14a, illuminatable element 14b as well as the audible indicating element such as horn 16 can be appropriately activated by the processor 30 in response to sensed combustive or explosive vapors to provide a visual or audible warning to the wearer or carrier of the detector 10 as to the presence of the sensed dangerous condition. The detector 10 can be energized using battery 36. It will be understood that the enclosure 12 seals the components of the detector 10 from the ambient atmosphere, except for the ingress and egress of ambient atmosphere, including the vapors of interest, via filter 22.

Processor 30 can also execute pre-stored instructions for monitoring the condition and operation of the detector 10. Trouble indicators can be presented visually, via displays 14a, b. Alternately, trouble indicators can also be provided verbally, via transducer 16. Remaining life-time or end of life indicators can be presented visually and audibly.

Figure 6B:
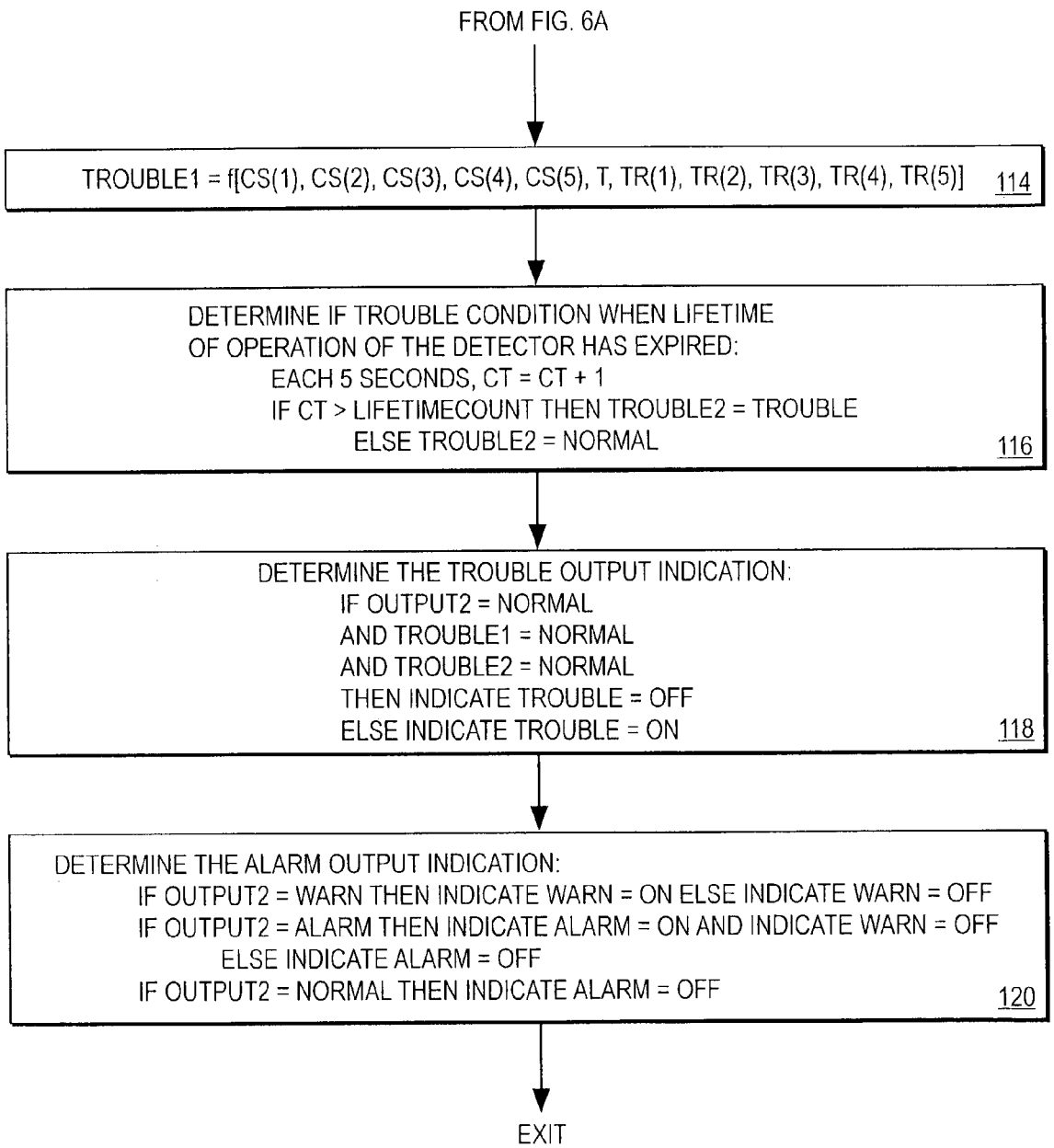
FIGS. 6A, B, taken together, are a flow diagram illustrating a process in accordance with the invention.

FIGS. 6A and 6B taken together illustrate a flow diagram of one form of processing of data by the detector 10. It will be understood that the methodology 100 of FIGS. 6A, B is exemplary only. The processing details are not a limitation of the present invention. Other forms of processing come within the spirit and scope of the invention.

Process 100 is entered in a step 102 wherein outputs from up to five different pluralities of polymeric-type sensors as well as an output from temperature compensating sensor, such as sensor 32a, are acquired. In a step 104, the output from the temperature sensor 32a is used to determine compensation coefficients associated with each of the pluralities of sensor outputs.

In a step 106, a plurality of compensated sensed outputs is formed for each of the members of the plurality of sensors S1, S2 . . . SN. In a step 108, an output signal is formed as a function of compensated sensed signals taking into account, if desired, cross-correlations.

In a step 110, the processed output signal, from step 108, is compared to one or more thresholds with each threshold representing an increasing percentage, for example of expected lowest combustible level of the gas or gases being sensed. If the processed output signal, Output 1, falls below the lowest pre-determined percentage threshold, a non-alarm or "normal" signal can be output. If the processed output signal, from step 108, exceeds an initial threshold L(1), then a "warning" signal can be output. Finally, in step 110, if the processed output signal from step 108 exceeds an alarm threshold L(2), an alarm signal can be output.

In step 112, analysis can be initiated as to whether or not a trouble condition is present at the detector. In step 114, where the compensated output signals, step 106, are not in a normal range, as expected or relative to other sensors, a trouble condition can be indicated. In step 116, the lifetime of the detector can be checked to determine if the expected lifetime of the detector has expired.

In a step 118, a determination can be made as to the absence of an out-of-range trouble condition, steps 112 and 114 or an end-of-lifetime condition step 116. In a step 120, an appropriate alarm indication dependent on the output of the threshold comparison steps 110 can be indicated.

Factory calibration of detectors such as detector 10 may be accomplished using at least one predetermined gas sample. If the polymer sensor(s) are exposed to a sample of each predetermined gas, then each sensor output signal can be measured and stored within the detector for use subsequently. Only one gas may need to be used in the factory for calibration purposes if the polymer sensor(s) produce repeatable signals.

Multiple gases can be used to characterize each polymer sensor(s) if they vary significantly in reproducibility and repeatability in signals. Combinations of gases in known proportions could be used.

The output signal(s) can be stored in the detector in the factory for characterization of each sensor. This information can be stored in non-volatile memory in the detector.

In summary, a disclosed portable combustible gas detector incorporates 1) polymer sensor(s) and non-polymer sensor(s) in combination, and 2) a filtering material to prevent liquid water and dust form reaching the sensor(s). An internal processor can execute mathematical routines to determine the amount of combustible gas detected and a display to indicate one or more of the amount of combustible gas, alarms, troubles, and replacement. The display may be visual or audible.

Disclosed detectors can be extremely small and be capable of being worn on a shirt, collar, hat, or pocket as appropriate with the clothing to maintain exposure to the environment. They can incorporate sealing elements in combination with an enclosure to seal circuitry from the environment. Such detectors may be inexpensive enough to be disposable after use. In such a case, the detector may have an internal timer (possibly with in the processor) that measures operation time and provides an output warning when the detector should be replaced. The executable instructions implement mathematical routines to compensate for the response characteristics of the sensors. A heater can be incorporated into the detector that is activated only under predetermined conditions, such as after an alarm. Factory calibration, where predetermined gases are exposed to the polymer sensor(s), can provide information to be downloaded and stored in the respective detector for subsequent use.

From the foregoing, it will be observed that numerous variations and modifications may be effected without departing from the spirit and scope of the invention. It is to be understood that no limitation with respect to the specific apparatus illustrated herein is intended or should be inferred. It is, of course, intended to cover by the appended claims all such modifications as fall within the scope of the claims.

What is claimed is:

1. A portable combustible gas detector for sensing at least one combustible gas, the detector comprising:

an array of polymer-type sensors, the sensors respond primarily to a predetermined combustible gas and generate at least one of, different signals for the same concentration of gas, or, similar signals for the same concentration of gas;

a filter positioned between the at least one polymer sensor and the environment;

a processor with an input to receive the signals from the sensors, the processor makes a determination of gas concentration;

the processor includes at least one output port coupled to an indicating device to provide an indication of the concentration of the predetermined combustible gas wherein a solid metal condenser is carried between the filter and polymer-type sensors to remove water vapors that pass through the filter;

an enclosure which contains the array, the filter the processor, the indicating device and the condenser where the enclosure provides an opening for an inflow of ambient atmosphere; and a region defined in the enclosure for at least selected components where the region is sealed from the condenser.

2. A detector as in claim 1 wherein the condenser comprises metal that has a relatively high mass and thermal conductivity.

3. A portable combustible gas detector for sensing at least one combustible gas, the detector comprising:

an enclosure;

a plurality of different polymer-type gas sensors, the sensors primarily respond to a single, predetermined combustible gas, with sensors of the plurality generating different signals for the same concentration of the predetermined gas;

at least one non-polymer sensor that senses a condition different than gas and generates a signal indicative thereof;

a filter positioned between the polymer-type sensors and the environment;

a processor with an input to receive the signals from all of the sensors, the processor makes a determination of concentration of the predetermined gas;

the processor includes at least one output port coupled to an indicating circuit to provide an indication of the concentration of the combustible gas.

4. A detector as in claim 3 wherein the gas is selected from a class of gases having an optical absorption peak in a wavelength between 3 microns and 4 microns.

5. A detector as in claim 4 wherein the at least one non-polymer sensor includes a temperature sensor.

6. A detector as in claim 5 wherein the temperature sensor includes a thermistor.

7. A detector as in claim 4 wherein the at least one non-polymer sensor includes a humidity sensor.

8. A detector as in claim 4 wherein the at least one non-polymer sensor includes a pressure sensor.

9. A portable combustible gas detector for sensing at least one combustible gas, the detector comprising:

an enclosure;

a plurality of different polymer-type gas sensors, the sensors primarily respond to a single, predetermined combustible gas with sensors of the plurality generating similar signals for the same concentration of the combustible gas;

at least one non-polymer sensor that senses a condition different than gas and generates at least a second signal indicative thereof;

a filter positioned between the at least one polymer sensor and the environment;

a processor with an input to receive the signals from all of the sensors, the processor makes a determination concentration of the combustible gas;

the processor includes at least one output port coupled to an indicating circuit to provide an indication of the concentration of the predetermined combustible gas.

10. A portable combustible gas detector comprising:

an enclosure;

a first plurality of polymeric sensors, the sensors primarily respond to a first combustible gas;

a second plurality of polymeric sensors, the sensors of the second plurality primarily respond to a second, different combustible gas;

a filter positioned between the polymeric sensors and an external environment;

a processor coupled to at least the sensors of the first and second pluralities;

where the processor compares sensor outputs to respective sets of multiple levels with each indicating a different concentration of the respective gas.

11. A detector as in claim 10 wherein the filter comprises a membrane-type material that passes the selected gas but resists passage of liquid water.

12. A detector as in claim 11 wherein the membrane-type material comprises, at least in part, a polymer-type material.

13. A detector as in claim 11 wherein the membrane-type material comprises a water excluding weave of material.

14. A detector as in claim 10 wherein the enclosure carries an elastic, water excluding sealing element.

15. A detector as in claim 10 which includes pre-stored polymer sensor time based performance monitoring instructions executable by the processor.

16. A detector as in claim 10 which includes pre-stored polymer sensor time based lifetime monitoring instructions executable by the processor.

* * * * *